US006559347B2

(12) United States Patent
Welker et al.

(10) Patent No.: US 6,559,347 B2
(45) Date of Patent: May 6, 2003

(54) DIELS-ADLER ADDUCTS OF EPOXYBUTENE AND EPOXYBUTENE DERIVATIVES

(75) Inventors: Mark E. Welker, Clemmons, NC (US); Marion A. Franks, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 10/071,700

(22) Filed: Feb. 8, 2002

(65) Prior Publication Data

US 2002/0173668 A1 Nov. 21, 2002

Related U.S. Application Data

(62) Division of application No. 09/591,587, filed on Jun. 9, 2000, now Pat. No. 6,380,447.

(51) Int. Cl.$^7$ .......................... C07C 2/50; C07D 307/00
(52) U.S. Cl. ........................................ 585/361; 549/459
(58) Field of Search ............................ 585/361; 549/459

(56) References Cited

U.S. PATENT DOCUMENTS

| 2,616,899 A | 11/1952 | Ladd ........................... 260/348 |
| 3,277,036 A | 10/1966 | Whitworth, Jr. et al. ...... 260/23 |
| 3,494,897 A | 2/1970 | Reding et al. ............. 260/78.5 |
| 4,538,013 A | 8/1985 | Donike et al. ............... 585/361 |
| 4,665,247 A | 5/1987 | Dessau ....................... 585/361 |
| 5,260,498 A | 11/1993 | Ellison ....................... 585/361 |
| 5,565,069 A | * 10/1996 | Oi et al. ..................... 585/361 |
| 5,892,124 A | 4/1999 | Olivier et al. .............. 568/374 |
| 5,945,553 A | * 8/1999 | Kuber et al. ................ 585/361 |
| 6,093,865 A | * 7/2000 | Lattner et al. .............. 585/361 |
| 6,294,706 B1 | * 9/2001 | Bergstrom et al. .......... 585/361 |

OTHER PUBLICATIONS

Abstract: 34301 *Improving Adhesion between Poly(Dicyclopentadiene) and Carbon Fiber, 810/Research Disclosure,* Hercules Incorporated (Nov. 1992).
Godleski et al.; *Utilization of Butadiene Monoepoxide as a Dienophile., Technical Report,* pp. 1–4, (Aug. 10, 1989).
R. Morrison and R. Boyd, 27.8 *The Diels–Alder reaction (Chapter 27), Organic Chemistry (3d Ed 1973),* pp. 876–877.

* cited by examiner

*Primary Examiner*—Deborah C. Lambkin
(74) *Attorney, Agent, or Firm*—Myers Bigel Sibley & Sajovec

(57) ABSTRACT

Diels-Alder adducts of dienophiles such as epoxybutene with dienes such as cyclopentadiene and cyclohexadiene are produced by carrying out the Diels-Alder reaction thereof at an elevated pressure. Addional dienophiles disclosed include 2,5-dihydrofuran and derivatives thereof; Additional dienes include isoprene and butadiene. Compounds produced from such reactions are also disclosed.

18 Claims, No Drawings

DIELS-ADLER ADDUCTS OF EPOXYBUTENE AND EPOXYBUTENE DERIVATIVES

RELATED APPLICATIONS

This application is a divisional of U.S. application Ser. No. 09/591,587 filed Jun. 9, 2000, U.S. Pat. No. 6,380,447, the contents of which are hereby incorporated by reference as if recited in full herein.

FIELD OF THE INVENTION

The present invention concerns Diels-Alder reactions of epoxybutene and derivatives thereof, and compounds produced from such reactions.

BACKGROUND OF THE INVENTION

U.S. Pat. No. 2,616,899 to Ladd reports the Diels-Alder reaction of hexachlorocyclopentadiene with epoxybutene (EpB). The Diels-Alder product was found to be a flame retardant and a stabilizer for polyvinyl chloride (PVC).

In 1989, a Kodak Research Laboratories technical report described the screening of various dienes in Diels-Alder reactions with EpB. Most reactions, including that with cyclopentadiene, produced none of the desired cycloaddition adduct. Only EpB reacted with diphenylisobenzofuran to produce a Diels-Alder cycloadduct, at 38% yield.

Cyclic compounds are useful for a variety of purposes, including the production of polymers and copolymers as described in U.S. Pat. No. 3,277,036 to Whitworth and Zutty and U.S. Pat. No. and 3,494,897 to Reding et al. Accordingly, there is a need for new ways to carry out, the Diels-Alder reaction, and a need for products thereof.

SUMMARY OF THE INVENTION

The Diels Alder reaction of certain dienes with certain dienophiles, when carried out under pressure, can be utilized to produce cyclic and bicyclic compounds described herein.

Accordingly, a first aspect of the present invention is a method of making a bicyclic compound selected from the group consisting of compounds of Formula X and compounds of Formula XI:

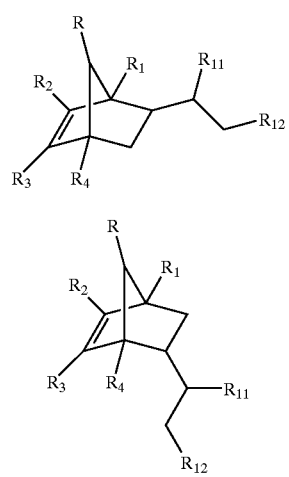

wherein:

R, $R_1$, $R_2$, $R_3$, and $R_4$ are each independently selected from the group consisting of H, and C1–C4 lower alkyl; and $R_{11}$ and $R_{12}$ each independently represent —H, —OH, —OCOCH$_3$, —OCH$_2$C$_6$H$_5$, or —OR$_{13}$ wherein $R_{13}$ represents C1–C4 lower alkyl, or $R_{11}$ and $R_{12}$ together represent —O—, —O—C(O)—O— or —O—C(CH$_3$)$_2$—O—; comprising reacting a diene according to Formula I:

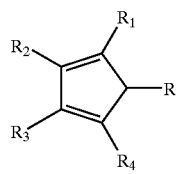

wherein R, $R_1$, $R_2$, $R_3$, and $R_4$ are as given above with a dieneophile according to Formula VI:

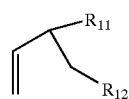

wherein $R_{11}$ and $R_{12}$ are as given above in a Diels-Alder reaction at a pressure greater than atmospheric pressure to yield a compound selected from the group consisting of compounds of Formula X and compounds of Formula XI.

A second aspect of the invention is a method of making a bicyclic compound selected from the group consisting of compounds of Formula XII and Formula XIII:

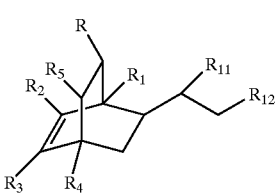

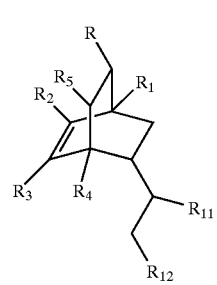

wherein:

R, $R_1$, $R_2$, $R_3$, $R_4$ and $R_5$ are each independently selected from the group consisting of H, and C1–C4 lower alkyl; and $R_{11}$ and $R_{12}$ each independently represent —H, —OH, —OCOCH$_3$, —OCH$_2$C$_6$H$_5$, or —OR$_{13}$ wherein $R_{13}$ represents C1–C4 lower alkyl, or $R_{11}$ and $R_{12}$ together represent —O—, —O—C(O)—O— or —O—C(CH$_3$)$_2$—O—; comprising reacting a diene according to Formula II:

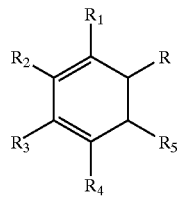
(II)

wherein R, $R_1$, $R_2$, $R_3$, $R_4$ and $R_5$ are as given above with a dieneophile according to Formula VI:

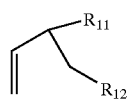
(VI)

wherein $R_{11}$ and $R_{12}$ are as given above in a Diels-Alder reaction at a pressure greater than atmospheric pressure to yield a compound selected from the group consisting of compounds of Formula XII and compounds of Formula XIII.

A third aspect of the present invention is a method of making a compound selected from the group consisting of compounds of Formula XIV and Formula XV:

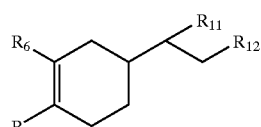
(XIV)

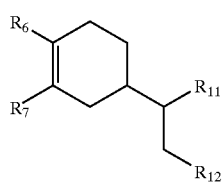
(XV)

wherein:

$R_6$ is —H;

$R_7$ is —H or —$CH_3$; and $R_{11}$ and $R_{12}$ each independently represent —H, —OH, —$OCOCH_3$, —$OCH_2C_6H_5$, or —$OR_{13}$ wherein $R_{13}$ represents C1–C4 lower alkyl, or $R_{11}$ and $R_{12}$ together represent —O—, —O—C(O)—O— or —O—C($CH_3$)$_2$—O—; comprising reacting a diene of Formula III or Formula IV:

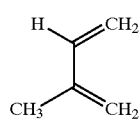
(III)

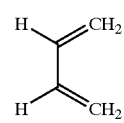
(IV)

with a dieneophile according to Formula VI:

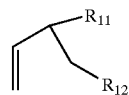
(VI)

wherein $R_{11}$ and $R_{12}$ are as given above in a Diels-Alder reaction at a pressure greater than atmospheric pressure to yield a compound selected from the group consisting of compounds of Formula XII and compounds of Formula XIII.

A further aspect of the present invention is a method of making a bicyclic compound selected from the group consisting of compounds of Formula XVI and compounds of Formula XVII:

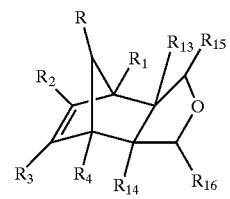
(XVI)

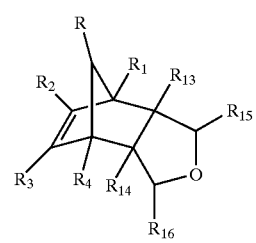
(XVII)

wherein R, $R_1$, $R_2$, $R_3$, $R_4$, $R_{13}$, $R_{14}$, $R_{15}$ and $R_{16}$ are each independently selected from the group consisting of H, and C1–C4 lower alkyl; comprising reacting a diene according to Formula I:

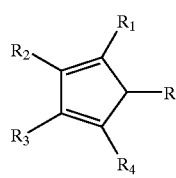
(I)

wherein R, $R_1$, $R_2$, $R_3$, and $R_4$ are as given above with a dieneophile according to Formula VII:

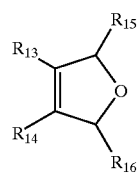
(VII)

wherein $R_{13}$, $R_{14}$, $R_{15}$ and $R_{16}$ are as given above in a Diels-Alder reaction at a pressure greater than atmospheric pressure to yield a compound selected from the group consisting of compounds of Formula XVI and compounds of Formula XVII.

A still further aspect of the present invention is a method of making a bicyclic compound selected from the group consisting of compounds of Formula XVII and compounds of Formula XIX:

(XVIII)

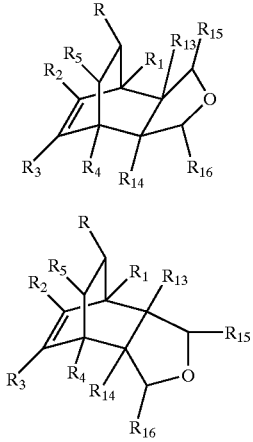

(XIX)

wherein R, $R_1$, $R_2$, $R_3$, $R_4$, $R_5$, $R_{13}$, $R_{14}$, $R_{15}$ and $R_{16}$ are each independently selected from the group consisting of H, and C1–C4 lower alkyl; comprising reacting a diene according to Formula II:

(II)

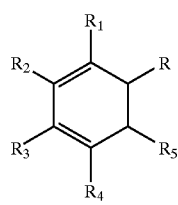

wherein R, $R_1$, $R_2$, $R_3$, $R_4$ and $R_5$ are as given above with a dieneophile according to Formula VII:

(VII)

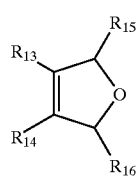

wherein $R_{13}$, $R_{14}$, $R_{15}$ and $R_{16}$ are as given above in a Diels-Alder reaction at a pressure greater than atmospheric pressure to yield a compound selected from the group consisting of compounds of Formula XVIII and compounds of Formula XIX.

A still further aspect of the invention is a method of making a compound according to Formula XX (XX)

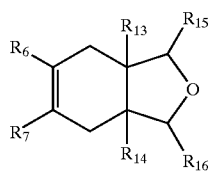

wherein $R_6$ is —H, $R_7$ is —H or —$CH_3$, and $R_{13}$, $R_{14}$, $R_{15}$ and $R_{16}$ are each independently selected from the group consisting of H and C1–C4 alkyl;

comprising reacting a diene of Formula III or Formula IV:

(III)

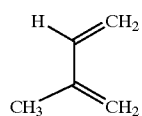

(IV)

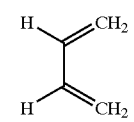

with a dieneophile according to Formula VI:

(VII)

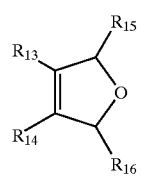

wherein $R_{13}$, $R_{14}$, $R_{15}$ and $R_{16}$ are as given above in a Diels-Alder reaction at a pressure greater than atmospheric pressure to yield a compound of Formula XX.

The present invention also provides compounds, particularly novel compounds, produced by the methods described above.

DETAILED DESCRIPTION OF THE PREFERRED EMBODIMENTS

The present invention concerns the reaction of certain dienes as described below with epoxybutene or epoxybutene derivatives as a dienophile, as also described below, to form cyclic product compounds as described below.

A. Dienes.

Dienes that may be used to carry out the present invention include isoprene, butadiene, cyclohexadiene, cyclopentadiene, and derivatives thereof.

Cyclopentadiene, cyclohexadiene and derivatives thereof that may be used to carry out the present invention are illustrated by Formulas I and II below:

(I)

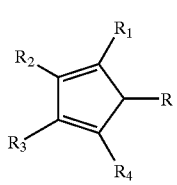

(II)

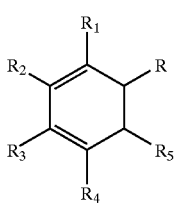

R, $R_1$, $R_2$, $R_3$, $R_4$ and $R_5$ are each independently selected from the group consisting of H, and C1–C4 lower alkyl.

Isoprene and butadiene, which may also be used as dienes to carry out the present invention, are illustrated by Formulas III and IV below:

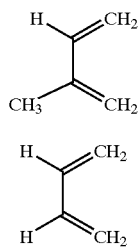

(III)

(IV)

B. Dienophiles.

The present invention may be carried out with epoxybutene (EpB) as the dienophile, which has the structure according to Formula V below, or EpB and derivatives thereof which are generally represented by Formula VI below:

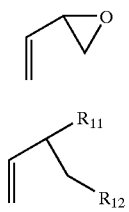

(V)

(VI)

$R_{11}$ and $R_{12}$ in Formula VI, may together represent —O—, in which case Formula VI represents epoxybutene as shown in Formula V. $R_{11}$ and $R_{12}$ may also represent —O—C(O)—O— or —O—C(CH$_3$)$_2$—O—, each of which forms a five member ring system. Such compounds are epoxybutene derivatives.

In addition, $R_{11}$ and $R_{12}$ may each independently represent —H, —OH, —OAc (—OCOCH$_3$), —OBz (—OCH$_2$C$_6$H$_5$), or —OR$_{13}$ wherein $R_{13}$ represents C1–C4 lower alkyl, preferably methyl. In particular preferred embodiments of formula VI above, $R_{11}$ is —H and $R_{12}$ is —OH;
$R_{11}$ is —OAc and $R_{12}$ is —OAc;
$R_{11}$ is —OR$_{13}$ $R_{12}$ is —OAc;
$R_{11}$ is —OBz and $R_{12}$ is —OH; and
$R_{11}$ is —OH and $R_{12}$ is —OH.

Still further dienophiles that may be used to carry out the present invention are compounds of Formula VII:

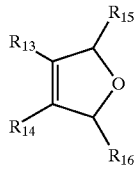

(VII)

In which $R_{13}$, $R_{14}$, $R_{15}$ and $R_{16}$ are each independently selected from the group consisting of H and C1–C4 lower alkyl.

C. Reaction Conditions.

The Diels-Alder reaction may be carried out in any suitable solvent, typically an organic solvent and typically an inert solvent, (e.g., a polar or nonpolar organic solvent), and preferably an aprotic solvent, such as toluene, tetrahydrofuran (THF), etc., or by heating the reactants together without a solvent.

The reaction may be carried out at any suitable temperature, typically in the range of about 65, 100 or 150 to 230, 250, or 300 degrees Celsius or more.

The time of the reaction is not critical, and may be carried out for from about 1 or 2 hours to 10, 20 or 100 hours or more. The reaction may be carried out as a batch reaction or as a continuous reaction.

The reaction may be carried out any suitable pressure, but is preferably carried out at a pressure greater than atmospheric pressure. For example, the reaction may be carried out at a pressure of from at least about 2, 4, 6 or 8 or 10 atmospheres to about 14, 18, 20, 30, 100, 1,000 or even 10,000 atmospheres or more.

If desired, the reaction may be catalyzed by the addition of a Lewis acid or other suitable catalyst, in accordance with known techniques.

Either the diene or the dienophile may be present in the reaction in excess amounts, or approximately equimolar amounts of the two reactants may be used. As is known in the literature, dicyclopentadiene may be used at reaction temperatures sufficiently high (e.g., above about 150 degrees C.) to produce free cyclopentadiene from its dimer.

The reactions described herein can produce either single isomeric products or mixtures of exo/endo isomers, depending on the substrate structures and reaction conditions. Where mixtures of compounds are formed the pure compounds can be isolated from those mixtures in accordance with known techniques.

D. Reaction Products.

A variety of different reaction product compounds may be produced by the reactions described herein, depending upon the choice of diene, dienophile, and reaction conditions.

In general, reaction product compounds of the present invention where the diene in the reaction is cyclopentadiene or a derivative thereof according to Formula I, are compounds of Formula X and Formula XI below. (Note that Formulas herein are intended to cover both the exo and endo forms of the compounds. Stereochemistry is not shown in the compounds, but the present invention is intended to encompass both enantiomerically pure compounds as well as racemic and other mixtures of isomers).

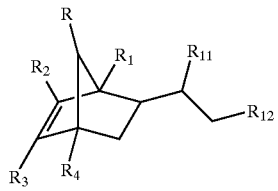

(X)

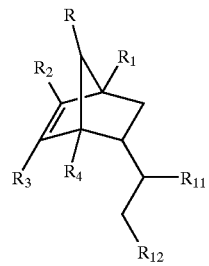

(XI)

In Formulas X and XI, R, $R_1$, $R_2$, $R_3$, $R_4$, $R_{11}$, and $R_{12}$ are as described above in connection with diene and dienophile reactants. In one embodiment, compounds of Formulas X and XI, are subject to the proviso that, when $R_1$, $R_2$, $R_3$, and $R_4$ are each H, then $R_{11}$ and $R_{12}$ are not together —O—. Alternatively stated, in compounds of Formulas X and XI, when $R_{11}$ and $R_{12}$ together represent —O—, then at least one of $R_1$, $R_2$, $R_3$, and $R_4$ is not H.

Reaction product compounds of the present invention, where the diene in the reaction is cyclohexadiene or a derivative thereof according to Formula II, are compounds of Formula XII and Formula XIII:

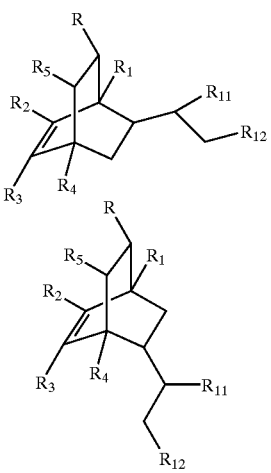

(XII)

(XIII)

In Formulas XII and XIII, R, $R_1$, $R_2$, $R_3$, $R_4$, $R_5$, $R_{11}$, and $R_{12}$ are as described above in connection with diene and dienophile reactants.

Reaction product compounds of the present invention, where the diene in the reaction is isoprene or isobutadiene, are compounds of Formula XIV and Formula XV:

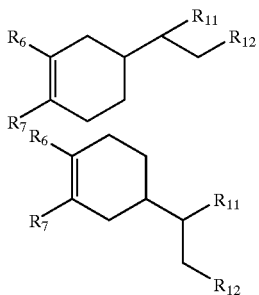

(XIV)

(XV)

In Formulas XIV and XV, $R_{11}$ and $R_{12}$ are as described above in connection with dienophile reactants. $R_6$ is —H, and $R_7$ is —H or —$CH_3$ (for butadiene or isoprene reactants, respectively).

Reaction product compounds of the present invention, where the dienophile is a compound of Formula VII above and the diene is a compound of Formula I above, include compounds of Formulas XVI and XVII:

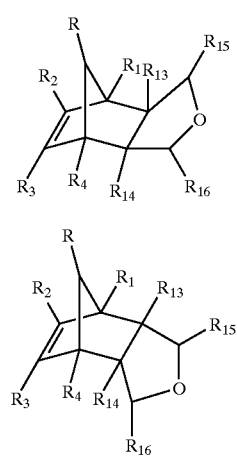

(XVI)

(XVII)

In Formulas XVI and XVII above, R, $R_1$, $R_2$, $R_3$, $R_4$, $R_{13}$, $R_{14}$, $R_{15}$, and $R_{16}$ are as described above in connection with diene and dienophile reactants.

Reaction product compounds of the present invention, where the dienophile is a compound of Formula VII above and the diene is a compound of Formula II above, include compounds of Formulas XVIII and XIX:

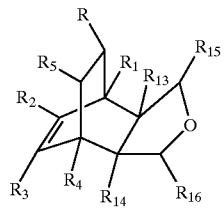

(XVIII)

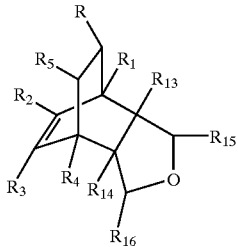

(XIX)

In Formulas XVIII and XIX above, R, $R_1$, $R_2$, $R_3$, $R_4$, $R_5$, $R_{13}$, $R_{14}$, $R_{15}$ and $R_{16}$ are as described above in connection with diene and dienophile reactants.

Reaction product compounds of the present invention, where the dienophile is a compound of Formula VII above and the dienes isoprene or butadiene as set forth in Formulas III–IV above, are given in Formula XX:

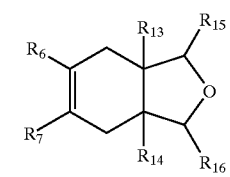

(XX)

In Formula XX, $R_{13}$, $R_{14}$, $R_{15}$ and $R_{16}$ are as described above in connection with the dienophile reactant. $R_6$ is H, and $R_7$ is —H or —$CH_3$ (for butadiene or isoprene reactants, respectively).

E. Uses.

The reaction product compounds of the present invention are useful as monomers for the preparation of polymers (see, e.g., U.S. Pat. No. 3,494,897; U.S. Pat. No. 3,277,036) may be used as monomers in ring opening metathesis polymerizations (ROMP) to form polymers, and, where the monomers contain an epoxy group, may be used as monomers to form in epoxy polymers, which polymers may in turn be used for a variety of purposes, including but not limited to being formed into useful articles such as sinks, fasteners, and the like in accordance with known techniques. In addition, the compounds are useful as polymer additives for modifying the properties of polymers, as intermediates for the manufacture of physiologically active and pharmaceutically active compounds, including pesticides, fungicides, insecticides, etc., and are useful per se as pesticides, fungicides, and insecticides.

Particular reactions that may be used to carry out the present invention, and products thereof, are set forth in the following sections.

F. The Thermal Diels Alder Reactions of Epoxybutene and Derivatives Thereof with Cyclopentadiene.

Epoxybutene and its derivatives undergo the thermal Diels Alder reaction with selected dienes under appropriate conditions. For example, cyclopentadiene reacts with epoxybutene at 170° C. in a sealed tube to yield the expected cycloadducts in a endo to exo ratio of about 76:24 (Scheme 1).

Scheme 1

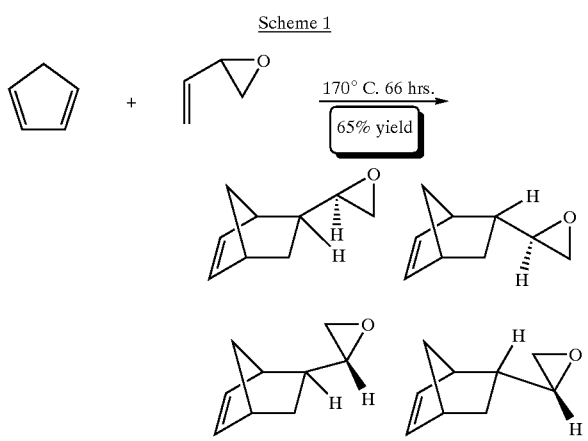

The reaction proceeds with the formation of more cycloadduct products when a large excess of dienophile and longer reaction times are used. The formation of dicyclopentadiene is prominent when using epoxybutene as the dienophile. This is possibly a result of the low reactivity of the dienophile. This problem can be overcome with the use of longer-reaction times.

Cyclopentadiene reacts with 2,5 dihydrofuran under similar conditions as those of epoxybutene to form the expected cycloadducts (Scheme 2).

Scheme 2

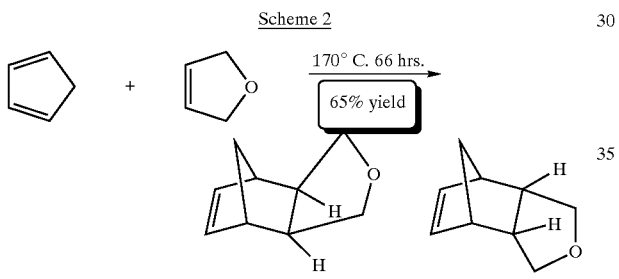

2,5 dihydrofuran is an ideal substrate for the study of these [4+2] cycloadditions because it doesn't have a preexisting chiral center. Therefore, we believe that the product shown in Scheme 2 is a good model for the NMR assignment of the endo and exo diastereomers.

Diagram 1

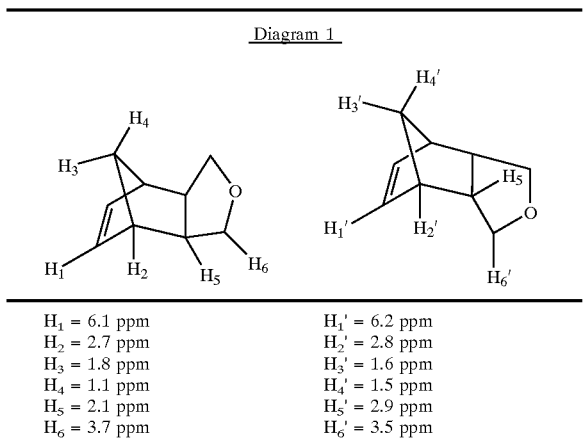

| | |
|---|---|
| $H_1$ = 6.1 ppm | $H_1'$ = 6.2 ppm |
| $H_2$ = 2.7 ppm | $H_2'$ = 2.8 ppm |
| $H_3$ = 1.8 ppm | $H_3'$ = 1.6 ppm |
| $H_4$ = 1.1 ppm | $H_4'$ = 1.5 ppm |
| $H_5$ = 2.1 ppm | $H_5'$ = 2.9 ppm |
| $H_6$ = 3.7 ppm | $H_6'$ = 3.5 ppm |

From Diagram 1, we noticed that the symmetry of the molecules allows us to unambigously assign the protons by region. We also notice that the differences in the exo and the endo structure are quite evident. The spectrum shows that the exo bridge protons ($H_3$ and $H_4$) are effected by the oxygen atom of the furan ring. The proton nearest the oxygen ($H_4$) is deshielded the most in comparison to it's endo isomer analog and the protons above the alkene (H3, H3') are shielded by the alkene anisotropy.

Cyclopentadiene also reacts with 3,4-diacetoxy-2-butene (Scheme 3). We have not yet determined the diastereomeric ratio for this mixture due to the inability to separate the diastereomers via GC. Nevertheless, we suspect the presence of both the endo and exo diastereomers as the product.

Scheme 3

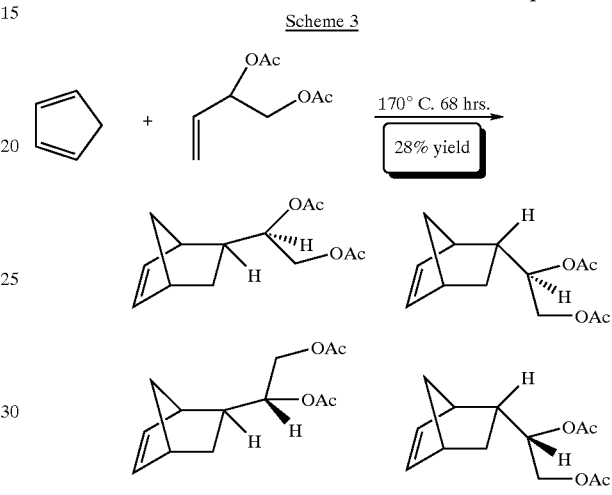

The reaction in Scheme 4 proceeded with a 95:5 ratio of endo to exo. Just as in the 2,5 dihydrofuran case, the lack of a preexisting chiral center insures the formation of only one set of possible diastereomeric products.

Scheme 4

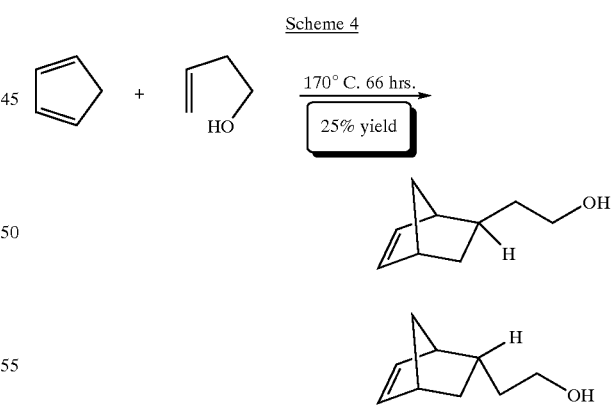

The reaction in Scheme 5 below proceeded with about a 1:1 ratio of endo to exo products. It is also noteworthy to observe the yield and reaction conditions of the 4-ethenyl-1,3 dioxolan-2-one. Milder heating and less reaction time produced 84% yield of cycloadducts. 4-Ethenyl-1,3 dioxolan-2-one is a better dienophile than the other dienophiles tested to date.

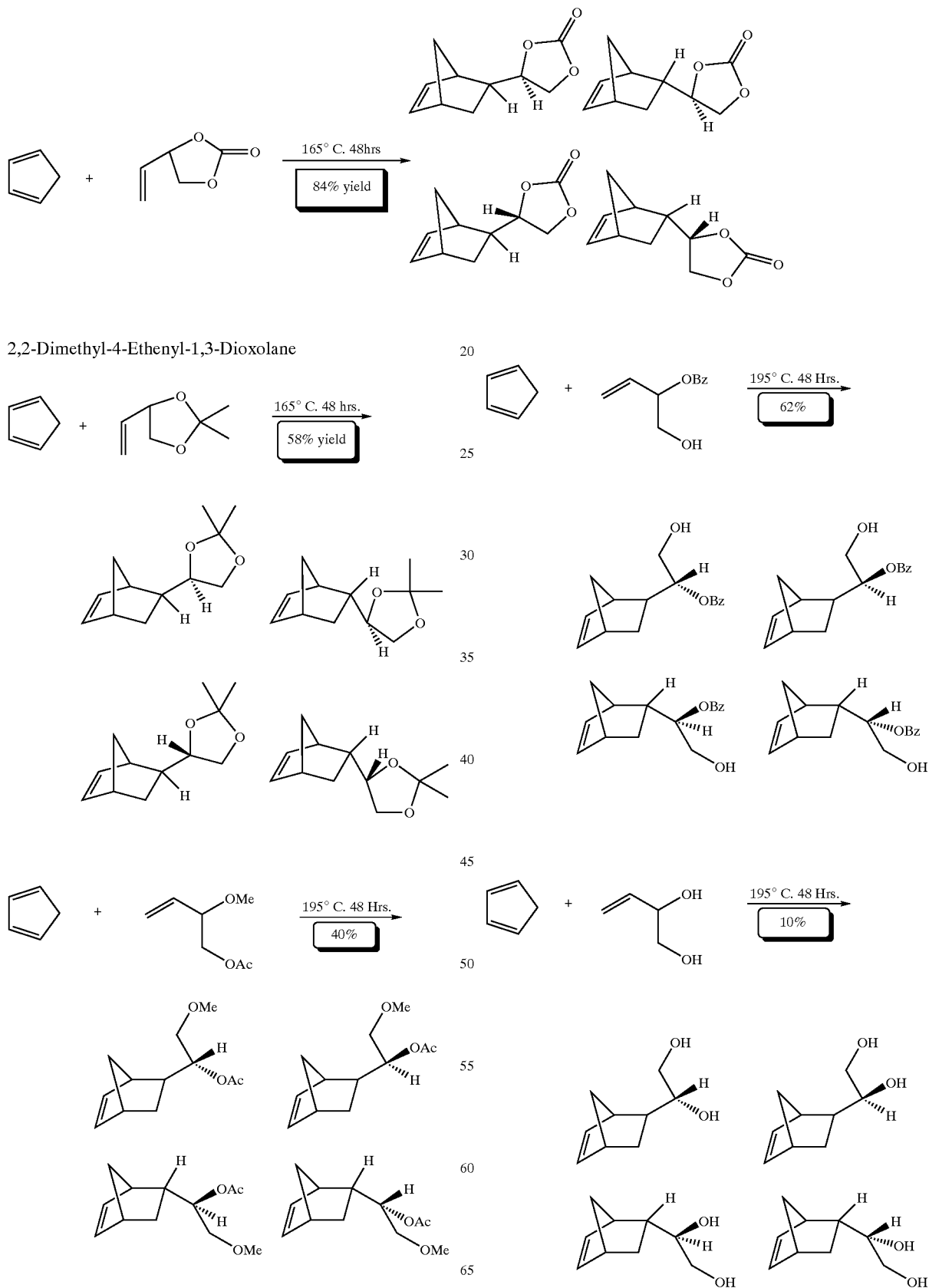
Scheme 5
2,2-Dimethyl-4-Ethenyl-1,3-Dioxolane

G. Other Thermal Diels-Alder Reactions.

Reactions with Cyclohexadiene:

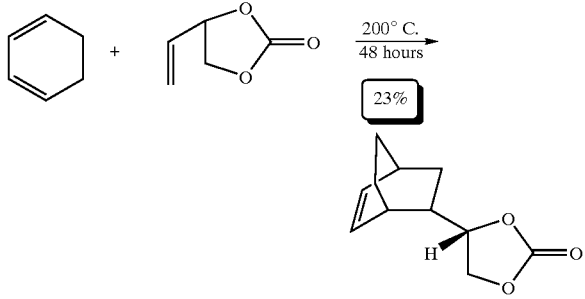

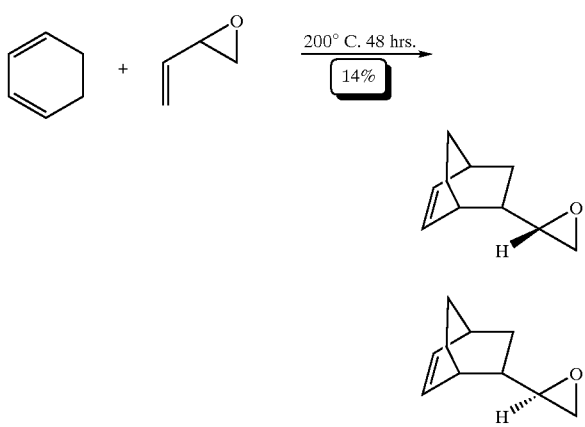

These compounds have been observed by ¹H NMR and GC/MS.

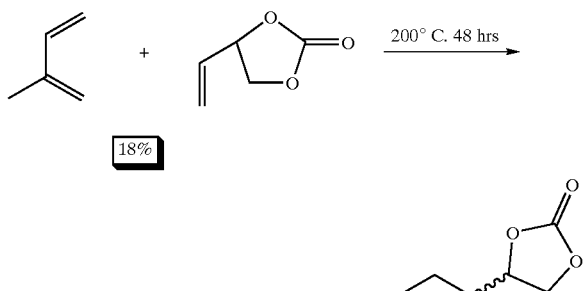

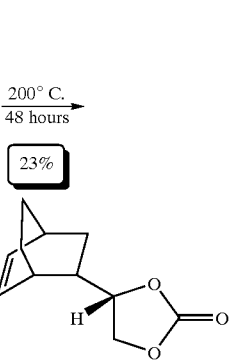

These isoprene reactions were maintained with a great excess of isoprene to dienophile. Under these conditions, we have noted that isoprene has a tendency to polymerize. Using hydroquinone only helped to catalyze the polymerization (possibly by H⁺ catalysis). Other radical scavengers may work better than hydroquinone. We also noted that even under longer reaction times, the yields were not as high as those that were observed in the cyclopentadiene case.

The present invention is explained in greater detail in the following non-limiting Examples.

EXAMPLES 1–9

Thermal Diels Alder Reactions of Epoxybutene and Derivatives Thereof with Cyclopentadiene

Example 1

Reaction Between Epoxybutene and Cyclopentadiene

A thick walled, high pressure tube (7 inch high pressure tube, Ace catalog number—8648-06 )was charged with freshly cracked cyclopentadiene (0.821 g, 12.42 mmol) and epoxybutene (8.21 g, 117.40 mmol). The contents were degassed by bubbling nitrogen gas through the solution for 15 minutes. The tube was equipped with a magnetic stirring bar and fitted with a Teflon screw cap. The reaction tube was placed into a oil bath set at 170° C. and the starting materials were allowed to react for 66 hours. The tube was then taken out of the oil bath and allowed to cool to room temperature. The yellow solution was transferred to a 10 ml conical reaction vial and equipped with a simple distillation apparatus. Epoxybutene (4.66 g, 66.49 mmol) was distilled from the solution at 63° C. The conical reaction vial was then connected to a micro spinning band distillation apparatus (Ace Catalog Number—9595-43). The distillation yielded 1.1 g (8.15 mmol, 65%) of a clear product at 75° C. (11 mmHg). The product contained 92% of the expected product and a 3% of dicyclopentadiene impurity. A second spinning band distillation at 75° C. (11 mmHg) yielded 0.470 g (3.45 mmol) of product not containing dicyclopentadiene.

Example 2

Reaction Between 2,5-dihydrofuran and Cyclopentadiene

A thick walled, high pressure tube was charged with freshly cracked cyclopentadiene (0.821 g 12.42 mmol) and 2,5 dihydrofuran (8.70 g, 124.13 mmol). The contents were degassed by bubbling nitrogen gas through the solution for 15 minutes. The tube was equipped with a magnetic stirring bar and fitted with a Teflon screw cap. The reaction tube was placed into a oil bath set at 170° C. and the starting materials were allowed to react for 66 hours. The tube was then taken out of the oil bath and allowed to cool to room temperature. The yellow solution was transferred to a 10 ml conical reaction vial and equipped with a simple distillation apparatus. 2,5-dihydrofuran (7.07 g, 100.87 mmol) was distilled from the solution at 64° C. The conical reaction vial was then connected to a micro spinning band distillation appa-

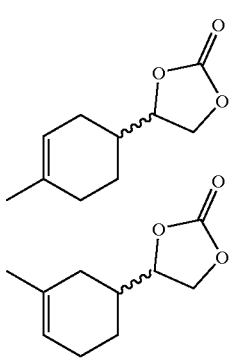

ratus. The distillation yielded 1.10 g (8.08 mmol, 65%) of a clear product at 70° C. (25 mmHg).

Example 3

Reaction Between 3-butenol and Cyclopentadiene

A thick walled, high pressure tube was charged with freshly cracked cyclopentadiene (0.821 g 12.42 mmol) and 3-butenol (8.84 g, 122.65 mmol). The contents were degassed by bubbling nitrogen gas through the solution for 5 minutes. The tube was equipped with a magnetic stirring bar and fitted with a Teflon screw cap. The reaction tube was placed into a oil bath set at 170° C. and the starting materials were allowed to react for 132 hours. The tube was then taken out of the oil bath and allowed to cool to room temperature. The solution was transferred to a 10 ml conical reaction flask and equipped with a simple distillation apparatus. 3-butenol (8.06 g, 111.83 mmol) was distilled from the solution at 113° C. The flask was then connected to a spinning band distillation apparatus. The distillation yielded 0.421 g (3.05 mmol, 25%) of a clear product at 62° C. (7 mmHg).

Example 4

Reaction Between 4-ethenyl-1,3 dioxolan-2-one and Cyclopentadiene

A thick walled, high pressure tube was charged with freshly cracked cyclopentadiene (0.411 g 6.21 mmol) and 4-ethenyl-1,3 dioxolan-2-one (5.59 g, 48.99 mmol). The contents were degassed by bubbling nitrogen gas through the solution for 5 minutes. The tube was equipped with a magnetic stirring bar and fitted with a Teflon screw cap. The reaction tube was placed into a oil bath set at 138° C. and the starting materials were allowed to react for 48 hours. The tube was then taken out of the oil bath and allowed to cool to room temperature. The tube was then cooled to −78° C. to relieve any built up pressure from the possible formation of $CO_2$. The yellow solution was transferred to a 25 ml round bottom flask and equipped with a vaccuum distillation apparatus. 4-ethenyl-1,3 dioxolan-2-one(3.78 g, 33.13 mmol) was distilled from the solution at 93° C. (11 mmHg). The conical reaction vial was then connected to a Kugelrhor distillation apparatus. The distillation yielded 1.12 g (5.55 mmol, 84%) of a clear product at 160° C. (5 mmHg).

Example 5

Reaction Between 3,4-diacetoxy-2-butene and Cyclopentadiene

A thick walled, high pressure tube was charged with freshly cracked cyclopentadiene (0.821 g 12.42 mmol) and 3,4-diacetoxy-2-butene(21.90 g, 127.21 mmol). The contents were degassed by bubbling nitrogen gas through the solution for 5 minutes. The tube was equipped with a magnetic stirring bar and fitted with a Teflon screw cap. The reaction tube was placed into a oil bath set at 170° C. and the starting materials were allowed to react for 66 hours. The tube was then taken out of the oil bath and allowed to cool to room temperature. The yellow solution was transferred to a 50 ml round bottom flask and equipped with a vaccuum distillation apparatus. 3,4-diacetoxybutene (11.83 g, 68.17 mmol) was distilled from the solution at 60° C. (9 mmHg). The flask was then connected to a Kugelrhor distillation apparatus. The distillation yielded 0.832 g (3.49 mmol, 28%) of a clear product at 180° C. (2 mmHg).

Example 6

Reaction Between 2,2-Dimethyl-4-ethenyl-1,3-dioxolane and Cyclopentadiene

A thick walled, high pressure tube was charged with freshly cracked cyclopentadiene (0.821 g, 12.42 mmol) and 2,2-Dimethyl-4-ethenyl-1,3-dioxolane (~10 g, ~78.02 mmol). The contents were degassed by bubbling nitrogen gas through the solution for 5 minutes. The tube was equipped with a magnetic stirring bar and fitted with a Teflon screw cap. The reaction tube was placed into a oil bath set at 165° C. and the starting materials were allowed to react for 66 hours. The tube was then taken out of the oil bath and allowed to cool to room temperature. The solution was transferred to a 25 mL flask and the excess 2,2-Dimethyl-4-ethenyl-1,3-dioxolane distilled using vacuum distillation (30° C., 11 mmHg). The distillation yielded 7.97 grams of 2,2-Dimethyl-4-ethenyl-1,3-dioxolane. The remainder of the solution in the flask was treated with bulb to bulb distillation yielding 1.39 grams (58%) of product at 120° C. (7 mmHg). The product was observed and it's identity confirmed by $^1$H NMR, $^{13}$C NMR, and HRMS.

Example 7

Reaction Between 3-Acetoxy-4-Methoxy-2-Butene and Cyclopentadiene

A thick walled, high pressure tube was charged with freshly cracked cyclopentadiene (0.821 g, 12.42 mmol) and 1-Acetoxy-2-Methoxy-3-Butene (7.08 g, 48.61 mmol). The contents were degassed by bubbling nitrogen gas through the solution for 5 minutes. The tube was equipped with a magnetic stirring bar and fitted with a Teflon screw cap. The reaction tube was placed into a oil bath set at 185° C. and the starting materials were allowed to react for 48 hours. The tube was then taken out of the oil bath and allowed to cool to room temperature. The solution was transferred to a 25 mL round bottom flask and the excess 1-Acetoxy-2-Methoxy-3-Butene distilled using vacuum distillation (68° C., 5 mmHg). The distillation yielded 3.80 grams of 1-Acetoxy-2-Methoxy-3-Butene. The remainder of the solution in the flask was treated with vacuum distillation yielding 1.049 grams (40%) of product at 129° C. (5 mmHg). The product was observed and it's identity confirmed by $^1$H NMR, $^{13}$C NMR, and EA.

Example 8

Reaction Between 4-Hydroxy-3-Benzyloxy-2-Butene and Cyclopentadiene

A thick walled, high pressure tube was charged with freshly cracked cyclopentadiene (0.841 g, 12.72 mmol) and 4-hydroxy-3-benzyloxy-2-butene (9.06 g, 50.92 mmol). The contents were degassed by bubbling nitrogen gas through the solution for 5 minutes. The tube was equipped with a magnetic stirring bar and fitted with a Teflon screw cap. The reaction tube was placed into a oil bath set at 185° C. and the starting materials were allowed to react for 48 hours. The tube was then taken out of the oil bath and allowed to cool to room temperature. The solution was transferred to a round bottom flask and the excess 1-Hydroxy-2-Benzyloxy-Butene distilled using vacuum distillation (105° C., 5 mmHg). The distillation yielded 3.48 grams of 1-Hydroxy-2-Benzyloxy-Butene. The remainder of the solution in the flask was treated with vacuum distillation yielding 1.924 grams (62%) of product at 189° C. (1 mmHg). The product was extracted using petroleum ether. The product was observed and it's identity confirmed by $^1$HNMR, $^{13}$CNMR, and HRMS.

Example 9

Reaction 3,4-Dihydroxy-2-Butene and Cyclopentadiene

A thick walled, high pressure tube was charged with freshly cracked cyclopentadiene (0.841 g, 12.72 mmol) and 3,4-dihydroxy-2-butene (5.24 g, 59.42 mmol). The contents were degassed by bubbling nitrogen gas through the solution for 5 minutes. The tube was equipped with a magnetic stirring bar and fitted with a Teflon screw cap. The reaction tube was placed into a oil bath set at 195° C. and the starting materials were allowed to react for 48 hours. The tube was then taken out of the oil bath and allowed to cool to room temperature. The solution was transferred to a 25 mL round bottom flask and the excess 3,4-dihydroxy-2-butene distilled using vacuum distillation (104° C., 12 mmHg). The distillation yielded 2.89 grams 3,4-Dihydroxy-2-butene. The remainder of the solution in the flask was treated with bulb to bulb distillation yielding 0.205 grams (10%) of product at 160° C. (1 mmHg).

EXAMPLES 10–13

Other Thermal Diels-Alder Reactions

Example 10

Reaction Between VEC and 1,3-Cyclohexadiene

A thick wall, high pressure tube was charged with vinyl ethenyl carbonate (0.982 g, 8.61 mmol), 1,3-cyclohexadiene (0.862 g, 10.77 mmol) and a magnetic stirring bar. The tube was degassed by bubbling nitrogen gas through the solution for 5 minutes, sealed using a Teflon screw cap, and placed into an oil bath set to 210° C. The reaction was stopped after 48 hours of heating and allowed to cool to room temperature. The solution was then placed into a 25 mL round bottom flask and distilled using bulb to bulb distillation. Heating at 182° C. (3 mmHg) removed the VEC from the product and the remaining product was a mixture of polymer and Product. The product was extracted into pet ether and filtered through Celite. The reaction yielded 0.322 g (23%) of product.

Example 11

Reaction Between 1,3-Cyclohexadiene and Epoxybutene

A thick walled high pressure tube was charged with Epoxybutene (9.00 g, 128.5 mmol), 1,3 cyclohexadiene (1.03 g, 12.92 mmol), and 15 ml of dry petroleum ether. The solution was briefly degassed and the tube was equipped with a stirring bar, Teflon cap, and placed into a oil bath set to 210° C. The reaction was allowed to proceed 72 hours, then the reaction was stopped and allowed to cool to room temp. The solution was placed into a 50 mL round bottom flask and evaporated using a using rotary evaporation. The product was dried using a high vacuum and again Pet Ether was added. A precipitate was formed and it was removed by filtration through Celite. The Pet Ether soluble product was concentrated using rotary evaporation and dried using vacuum. The collected product was weighed in a tared flask and the weight of the product was 0.279 g (14%).

Example 12

Reaction Between VEC and Isoprene

A thick wall, high pressure tube was charged with isoprene (8.51 g, 125 mmol) and vinyl ethenyl carbonate (0.800 g, 7.0 mmol). The solution was briefly degassed and the tube was equipped with a stirring bar, Teflon cap, and placed into a oil bath set to 210° C. The reaction was allowed to proceed of the course of 72 hours, then the reaction was stopped and allowed to cool to room temp. The isoprene was evaporated using using rotary evaporation. The reaction produced 0.273 g (18%) of product.

Example 13

Reaction Between 2,5 Dihydrofuran and Isoprene

A thick wall, high pressure tube was charged with isoprene (13.51 g, 198.3 mmol) and 2,5 dihydrofuran (0.927 g, 13.2 mmol). The solution was briefly degassed and the tube was equipped with a stirring bar, Teflon cap, and placed into a oil bath set to 215° C. The reaction was allowed to proceed of the course of 72 hours, then the reaction was stopped and allowed to cool to room temp. Excess isoprene was removed by using rotary evaporation. The product was obtained by bulb to bulb distillation at 91° C. (10 mmHg). The procedure produce 0.347 g (19%) of products.

The foregoing is illustrative of the present invention, and is not to be construed as limiting thereof. The invention is defined by the following claims, with equivalents of the claims to be included therein.

We claim:

1. A bicyclic compound selected from the group consisting of compounds of Formula X and compounds of Formula XI:

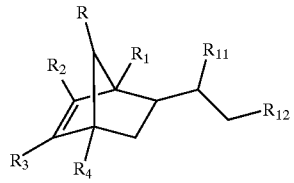

(X)

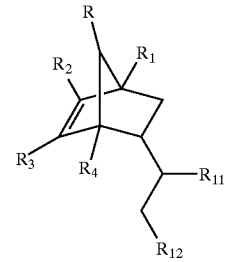

(XI)

wherein:

$R$, $R_1$, $R_2$, $R_3$, and $R_4$ are each independently selected from the group consisting of H, and C1–C4 lower alkyl; and $R_{11}$ and $R_{12}$ each independently represent —H, —OH, —OCOCH$_3$, —OCH$_2$C$_6$H$_5$, or —OR$_{13}$ wherein $R_{13}$ represents C1–C4 lower alkyl, or $R_{11}$ and $R_{12}$ together represent —O—, —O—C(O)—O— or —O—C(CH$_3$)$_2$—O—;

subject to the proviso that, when $R_1$, $R_2$, $R_3$, and $R_4$ are each H, then $R_{11}$ and $R_{12}$ are not together —O—.

2. A compound according to claim 1, wherein $R_{11}$ and $R_{12}$ together represent —O—, —O—C(O)—O— or —O—C(CH$_3$)$_2$—O—.

3. A compound according to claim 1, wherein $R_{11}$ and $R_{12}$ together represent —O—.

4. A compound according to claim 1, wherein $R_{11}$ and $R_{12}$ each independently represent —H, —OH, —OCOCH$_3$, —OCH$_2$C$_6$H$_5$, or —OR$_{13}$ wherein $R_{13}$ represents C1–C4 lower alkyl.

5. A compound according to claim 1, wherein R, $R_1$, $R_2$, $R_3$, and $R_4$ are each H; and $R_{11}$ and $R_{12}$ are each H.

6. A bicyclic compound selected from the group consisting of compounds of Formula XII and Formula XIII:

(XII)

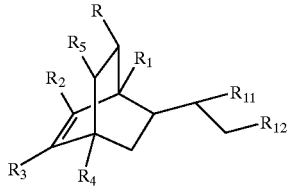

(XIII)

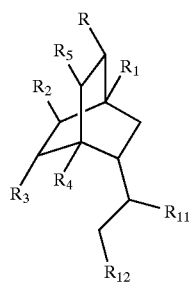

wherein:

R, $R_1$, $R_2$, $R_3$, $R_4$ and $R_5$ are each independently selected from the group consisting of H, and C1–C4 lower alkyl; and $R_{11}$ and $R_{12}$ each independently represent —H, —OH, —OCOCH$_3$, —OCH$_2$C$_6$H$_5$, or —OR$_{13}$ wherein $R_{13}$ represents C1–C4 lower alkyl, or $R_{11}$ and $R_{12}$ together represent —O—, —O—C(O)—O— or O—C(CH$_3$)$_2$—O—.

7. A compound according to claim 6, wherein $R_{11}$ and $R_{12}$ together represent —O—, —O—C(O)—O— or —O—C(CH$_3$)$_2$—O—.

8. A compound according to claim 6, wherein $R_{11}$ and $R_{12}$ together represent —O—.

9. A compound according to claim 6, wherein $R_{11}$ and $R_{12}$ each independently represent —H, —OH, —OCOCH$_3$, —OCH$_2$C$_6$H$_5$, or —OR$_{13}$ wherein $R_{13}$ represents C1–C4 lower alkyl.

10. A compound according to claim 6, wherein R, $R_1$, $R_2$, $R_3$, $R_4$ and $R_5$ are each H; and $R_{11}$ and $R_{12}$ are each H.

11. A bicyclic compound selected from the group consisting of compounds of Formula XVI and compounds of Formula XVII:

(XVI)

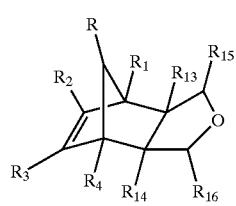

(XVII)

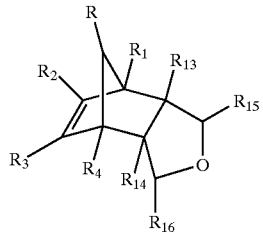

wherein R, $R_1$, $R_2$, $R_3$, $R_4$, $R_{13}$, $R_{14}$, $R_{15}$ and $R_{16}$ are each independently selected from the group consisting of H, and C1–C4 lower alkyl.

12. A compound according to claim 11, wherein R, $R_1$, $R_2$, $R_3$, and $R_4$ are each H.

13. A compound according to claim 11, wherein $R_{13}$, $R_{14}$, $R_{15}$ and $R_{16}$ are each H.

14. A compound according to claim 11, wherein wherein R, $R_1$, $R_2$, $R_3$, $R_4$, $R_{13}$, $R_{14}$, $R_{15}$ and $R_{16}$ are each H.

15. A bicyclic compound selected from the group consisting of compounds of Formula XVIII and compounds of Formula XIX:

(XVIII)

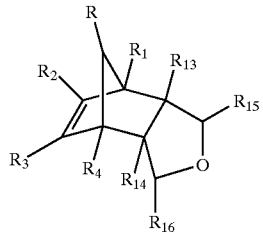

(XIX)

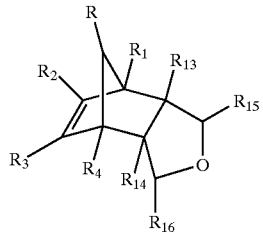

wherein R, $R_1$, $R_2$, $R_3$, $R_4$, $R_5$, $R_{13}$, $R_{14}$, $R_{15}$ and $R_{16}$ are each independently selected from the group consisting of H, and C1–C4 lower alkyl.

16. A compound according to claim 15, wherein R, $R_1$, $R_2$, $R_3$, $R_4$ and $R_5$ are each H.

17. A compound according to claim 15, wherein $R_{13}$, $R_{14}$, $R_{15}$ and $R_{16}$ are each H.

18. A compound according to claim 15, wherein wherein R, $R_1$, $R_2$, $R_3$, $R_4$, $R_{13}$, $R_{14}$, $R_{15}$ and $R_{16}$ are each H.

* * * * *

UNITED STATES PATENT AND TRADEMARK OFFICE
CERTIFICATE OF CORRECTION

PATENT NO. : 6,559,347 B2
DATED : May 6, 2003
INVENTOR(S) : Welker et al.

It is certified that error appears in the above-identified patent and that said Letters Patent is hereby corrected as shown below:

Title page,
Item [54], Title, should read -- DIELS-ALDER ADDUCTS OF EPOXYBUTENE AND EPOXYBUTENE DERIVATIVES --
Item [56], References Cited, OTHER PUBLICATIONS, the Morrison reference should read -- R. Morrison and R. Boyd, 27.8 *The Diels-Alder Reaction (Chapter 27), Organic Chemistry (3d Ed 1973), pp. 876-877.* --

Column 1,
Line 1, should read -- DIELS-ALDER ADDUCTS OF --

Column 22,
Line 22, should read -- 14. A compound according to claim 11, wherein --
Line 58, should read -- 18. A compound according to claim 15, wherein --

Signed and Sealed this

Twenty-fourth Day of February, 2004

JON W. DUDAS
*Acting Director of the United States Patent and Trademark Office*